United States Patent [19]

Bardsley et al.

[11] 4,338,032
[45] Jul. 6, 1982

[54] DETECTION OF FAULTS IN SHEET AND LIKE MATERIALS

[75] Inventors: Harold B. Bardsley, Euxton; Edward C. Lear, Turton, near Bolton; J. Robert Jones, Chadderton, all of England

[73] Assignee: Spencer Wright Industries, Inc., Chattanooga, Tenn.

[21] Appl. No.: 117,019

[22] Filed: Jan. 31, 1980

[30] Foreign Application Priority Data

May 18, 1979 [GB] United Kingdom ............... 7917452

[51] Int. Cl.³ ............................................. G01N 21/19
[52] U.S. Cl. .................................. 356/431; 250/572; 356/238
[58] Field of Search ............... 356/429, 430, 431, 238; 250/562, 563, 571, 572; 350/6.2, 6.3, 6.4; 74/55

[56] References Cited

U.S. PATENT DOCUMENTS

| | | | |
|---|---|---|---|
| 3,160,759 | 12/1964 | Ward | 356/430 |
| 3,305,687 | 2/1967 | Vinzelberg et al. | 250/563 |
| 3,308,658 | 3/1967 | Bryan | 250/563 |
| 3,589,816 | 6/1971 | Sugaya | 250/572 |
| 3,596,274 | 7/1971 | Heringhaus | 250/572 |
| 3,871,773 | 3/1975 | Shaw | 356/431 |
| 3,909,103 | 9/1975 | Graves et al. | 350/6.3 |

FOREIGN PATENT DOCUMENTS 1170179  11/1969  United Kingdom ............... 250/572

*Primary Examiner*—R. A. Rosenberger
*Attorney, Agent, or Firm*—Alan Ruderman

[57] ABSTRACT

Faults can be detected in sheet material, particularly in tufted fabric during manufacture of same, by scanning a surface of the material with an electrical scanning device which produces an electrical output representative of characteristics of the scanned surface. The electrical output is monitored to detect deviations from a norm representative of a fault condition. The scanning may be effected with a scanning device, comprising for example a light receiver which picks up reflected or transmitted light from the material, which is moved across the sheet transversely to the direction of advancement of the sheet.

6 Claims, 7 Drawing Figures

DETECTION OF FAULTS IN SHEET AND LIKE MATERIALS

BACKGROUND OF THE INVENTION

The invention concerns the detection of faults in sheet and like materials, and has particular, though not exclusive, reference to the detection of faults in tufted fabrics.

In the manufacture of tufted fabrics wherein multiple side-by-side lines of stitches are entered in a backing fabric by respective needles which repeatedly pierce such fabric and co-operate with oscillating loopers disposed at the opposite side of the fabric from the needles to form loops in the backing fabric, any malfunction in the operation of a needle/looper combination or fault in the yarn feed to a needle will manifest itself in a fault in the tufted fabric, which fault, by the nature of the construction of a tufted fabric, will continue along the line of stitching until remedied. Thus, for example, a broken yarn will give rise to a missing line of stitching, whilst a light or loose yarn or a poor knife action will result in some anomaly in the tuft or in the backstitch in the line of stitches in which the non-standard yarn relates.

Present day tufting machines operate at very high speed, and so much so that a fault which remains undetected for only a short time can give rise to an appreciable length of fabric which exhibits the fault. Bearing in mind that tufted fabrics are produced in widths of up to five meters, any appreciable length of faulty fabric which is produced represents a significant financial disadvantage to the producer.

SUMMARY OF THE INVENTION

The object of the present invention is to provide a method of and a means for detecting faults in sheet and like materials, with particular reference to tufted fabrics.

According to one aspect of the present invention there is proposed a method for detecting faults in sheet materials which comprises the steps of scanning a surface of the sheet material with an electrical scanning device which produces an electrical output representative of characteristics of said surface, and monitoring said electrical output to detect deviations from a norm representative of a fabric fault.

With this arrangement, in so far as the said characteristics of said sheet surface are monitored by monitoring of an electrical output, it will be appreciated that it is possible to detect and respond to the occurrence of a fabric fault quickly and conveniently.

The scanning of the sheet surface may be effected in any suitable manner and thus, for example, may be effected by exposing said surface to radiation such that the said surface characteristics influence transmission through, or reflection or refraction or modification of properties of the radiation by said surface. Electromagnetic radiation such as visible light, infra-red, radio waves or the like may be utilized. Alternatively it is possible to use other forms of radiation such as nuclear radiation or ultrasonic waves. In a particularly preferred embodiment visible (or infra-red) light is used and this is directed at the sheet surface so as to be reflected back therefrom to a suitable light (or infra-red) sensitive device; although in an alternative embodiment light is transmitted through the fabric between a visual light (or infra-red) source and an appropriate sensor arranged respectively on opposite sides of the fabric.

Instead of using radiation for scanning purposes it is possible to utilise other techniques involving for example electrostatic or capacitive sensors which are influenced by the thickness of the sheet (for example as it passes between the plates of a capacitor) or by the proximity of the said surface of the sheet to a fixed conductor or other body or device for example so as to define a capacitor therewith or so as to influence the existence or magnitude of a field associated therewith. It is even possible to utilise mechanical scanning techniques for example involving movement of a deflectable feeler in contact with said surface. Further, where appropriate, scanning may involve positioning of a suitable sensor in relation to said surface so as to receive emission from the sheet material at the surface, for example radiation emissions from radioactive trace elements incorporated in the sheet material.

The production of the said electrical output as a consequence of scanning of the said surface may be achieved in any suitable manner dependent on the scanning technique used. Thus, where radiation transmission, reflection or refraction is involved, the scanning device may incorporate a radiation receiver which produces the electrical output on receiving the transmitted, reflected or refracted radiation, such output being initiated or terminated and/or varying in magnitude in dependence on the presence or absence or degree of intensity of the transmission, reflection or refraction of the radiation. Accordingly, where visible (or infra-red) light is used the scanning device may comprise a light source (such as a filament lamp or light-emitting diode) and a light sensor (such as a photo-transistor, light-sensitive resistor, photo-voltaic cell or the like). Where the scanning technique involves modification of a property of radiation such as a frequency shift of same, the scanning device will incorporate an appropriate device capable of responding to such modification and converting same to a corresponding electrical output.

Where other scanning techniques are used, the scanning devices may incorporate appropriate other electrical signal-producing devices such as electronic bridge circuitry, electro-magnetic or piezo-electric transducers or the like.

Whilst the method of the invention may be applied to the detection of any suitable fault in any suitable kind of sheet material, preferably the method is applied to the detection of a fault arising from a broken or wrongly tensioned yarn occurring during manufacture of a tufted fabric. Thus the method of the invention may be applied during manufacture of such tufted fabric preferably by subjecting said fabric to continuous scanning with one or more scanning devices. Such continuous scanning may be effected by oscillating the or each scanning device backwards and forwards transversely across the sheet material during advance of the material.

Where the method is applied to fault detection during manufacture of a tufted fabric as mentioned above the monitored electrical output may be utilised to actuate an alarm and/or to actuate control equipment to effect automatic stopping of the tufting machine in the event that a fault is detected. Alternatively or additionally, the monitored electrical output may be utilised to produce a visual indication, such as an alpha-numerical display or print-out or the like, which both indicates the existence of a fault condition and also identifies the location of same.

In accordance with a second aspect of the present invention there is provided apparatus for detecting faults in an advancing sheet of fabric comprising a scanning device arranged to scan one surface of the sheet across the sheet transversely to said direction of advancement, said scanning device being arranged to produce an electrical output representative of characteristics of said surface, and a monitoring device connected to said scanning device so as to monitor said electrical output thereof and detect deviations from a norm representative of a fabric fault.

Preferably the scanning device is mounted on a support, such as a bar, which is oscillated continuously backwards and forwards. The movement of the support is preferably effected via a compact cam drive which is arranged to ensure smooth movement of the support and, in particular, smooth reversal of same without a rest point at the reversal position.

Preferably also, the monitoring device has a digital display which is arranged to produce a numerical indication in the event that a fault is detected, which indication identifies the position of the fault.

BRIEF DESCRIPTION OF THE DRAWINGS

The particular features, advantages and other objects of the invention will become apparent from the following description which is by way of example only, with reference to the accompanying drawings, and in which.

DESCRIPTION OF THE PREFERRED EMBODIMENTS

Figure 3:
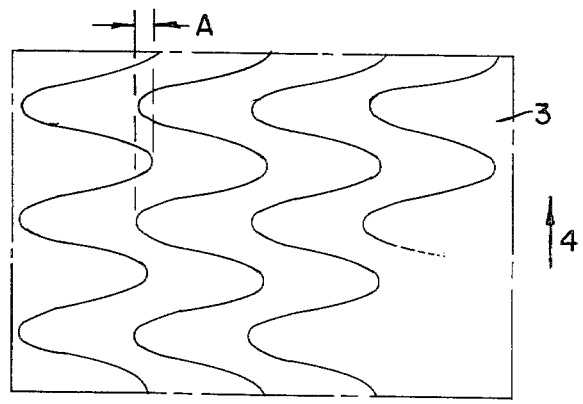
FIG. 3 is a plan view of a fabric showing the path of movement, relative to an advancing fabric, of scanning devices of the apparatus of FIG. 1.

Referring now to the drawings, apparatus for use in detecting faults in a tufted fabric, during manufacture of such fabric in a tufting machine, comprises a plurality of scanning devices 1 each oscillatable along a respective path of predetermined extent parallel to the back surface 2 of such fabric 3 and transversely to the direction of advancement 4 of the fabric (FIG. 3).

As illustrated three scanning devices 1 are shown although numbers significantly in excess of this are contemplated, the respective paths of oscillation of the scanning devices being such as to provide for a limited overlap A as between the paths of adjacent scanning devices at the extremes of movement thereof, as is indicated in FIG. 3.

In a typical arrangement each scanning device 1 will have a traverse of, say, three to twelve inches, and will oscillate at, say, five cycles per second.

Figure 1:
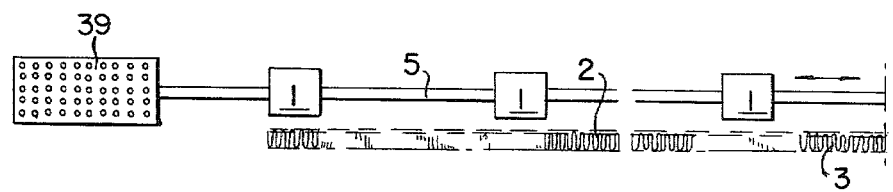
FIG. 1 is a diagrammatic section taken through one form of apparatus according to the invention for use in detecting faults in a tufted fabric.
Figure 2:
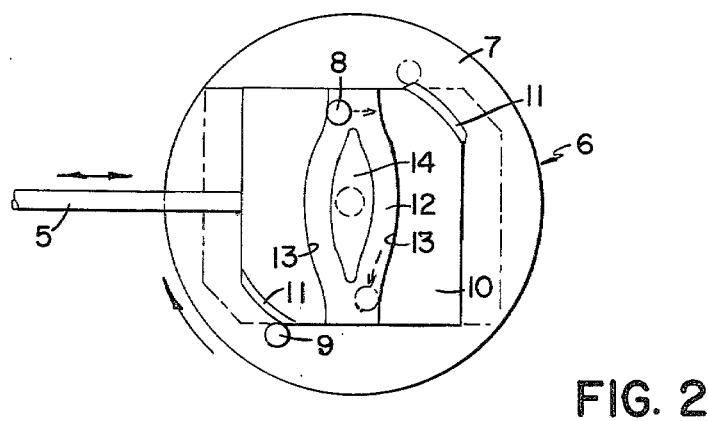
FIG. 2 is a diagrammatic side elevation to an enlarged scale of part of a cam drive used with the apparatus of FIG. 1.

The scanning devices 1 are secured to a common support bar 5 which is appropriately mounted so as to be longitudinally slidable backwards and forwards thereby to effect the aforesaid oscillation of the scanning devices 1. Movement of the bar 5 is achieved from an electrical motor via a cam drive 6 as shown in FIG. 2. The motor rotatably drives a disc 7 at constant speed and two rollers 8, 9 on the disc engage a cam plate 10. The plate 10 is of generally rectangular form and has convexly curved roller tracks 11 at two diametrically opposite corners thereof. In the central region of the plate there is a roller channel 12 with outwardly curved side walls 13 and a central island 14. The plate 10 is secured to the end of the support bar 5 and is free to move from side to side relative to the disc 7. As the disc 7 rotates, one roller 8 runs against first one then the other of the side walls 13 of the channel 12 thereby deflecting the plate 10 alternately in opposite directions. As the roller passes from one to the other of the side walls at the top and bottom ends of the channel 12, the roller 9 engages a respective one of the roller tracks 11 and applies a driving force thereto. Thus, the plate 10 (and hence the scanning devices 1) move smoothly backwards and forwards without jerking or vibration such as may damage or disturb the setting of the scanning devices or other equipment connected to the bar 5 as described hereinafter.

Figure 4:
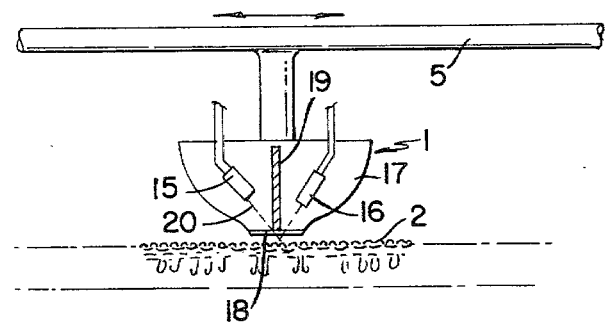
FIGS. 4 and 5 are diagrammatic sectional views of different embodiments of scanning devices for use in the apparatus of FIG. 1.

With reference to FIG. 4, each scanning device 1 may comprise a light emitter 15 (such as an LED operating in the visual or infra-red region) and a light detector 16 (such as a photo-transistor) mounted in an inverted mushroom or dome-shaped housing 17. The housing 17 has a flat transparent region 18 in the center of the underside thereof and the emitter 15 and the detector 16 are arranged respectively to transmit and receive light through this region 18, a screen 19 being interposed between the emitter and detector within the housing 17.

The scanning devices 1 of the kind shown in FIG. 4 are in use positioned such that the transparent regions 18 make sliding contact with the back surface 2 of the fabric 3, which back surface 2 constitutes the rear surface of the backing material of the fabric with rear portions of the yarn which have been needled through the backing material to define the tufts on the top surface thereof. The arrangement of the emitter 15 and the detector 16 within the housing 17 of each scanning device 1 (i.e. the spacing and angle of inclination of same) are such that light is reflected from the emitter 15 to the detector 16 from the backing material, with sufficient intensity to actuate the detector 16, in the regions between the yarns, but the light path 20 is blocked and actuation of the detector 16 is sharply cut off when a correctly inserted yarn is in alignment with the center of the transparent region 18.

Thus, with a fabric having no fault, the detector 16 of each scanning device 1 will produce a train of positive impulses corresponding to the spaces between alternate yarns. In the event that a missing yarn occurs during the traverse of any particular scanning device 1, the normal pattern of impulses will be disrupted and such disruption can be detected as described hereinafter.

By suitably arranging the rate of traverse of the scanning devices 1 in relation to the rate of feed of tufted fabric, the maximum period between successive passes across any given line of stitches, and thus the period for which a fault can remain undetected, can be determined. If the apparatus is positioned closely adjacent to the tufting position, the length of tufted product exhibiting the fault can be minimised, with consequential saving in the amount of substandard product.

Scanning of the backstitch side of the fabric as described above does provide for the possibility not only of detecting the absence of a backstitch in any instance, but also of detecting deviation from the norm of a backstitch which, though present, is not of a standard form, such a non-standard form arising for example from a poor cutting action (in the case of a cut-pile fabric) which gives rise to a pulling or undue tightening of the backstitch and a localised deformation of the surface configuration at the backstitch side of the fabric.

Figure 5:
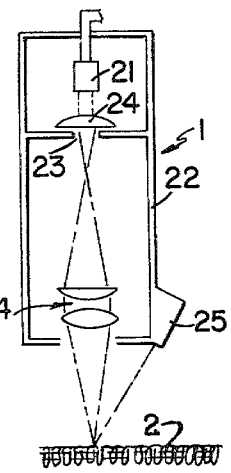

An alternative form of scanning device 1 is shown in FIG. 5. Such scanning device 1 is mounted on the bar 5 so as to be spaced from the surface 2 of the fabric 3. The device has a light-sensitive device 21 mounted at one end of focusing tube 22, the other end of such tube 22 being directed at the fabric surface 2 and appropriate optical components including, for example, a collimating slit 23 and lenses 24, being provided within the tube 22 so that light reflected from small regions of the surface 2 of the fabric, as scanned by the device 1, is sharply focused on the light sensor 21. Incident light is provided by a light source 25 directed at an angle onto the scanned region, which source 25 is mounted on the tube 22 internally or externally thereof. This scanning device 1 operates in like manner to the device of FIG. 4 and has the advantage that contact with the surface 2 is not required, although a lower level of output from the sensor 21 may result.

Figure 6:
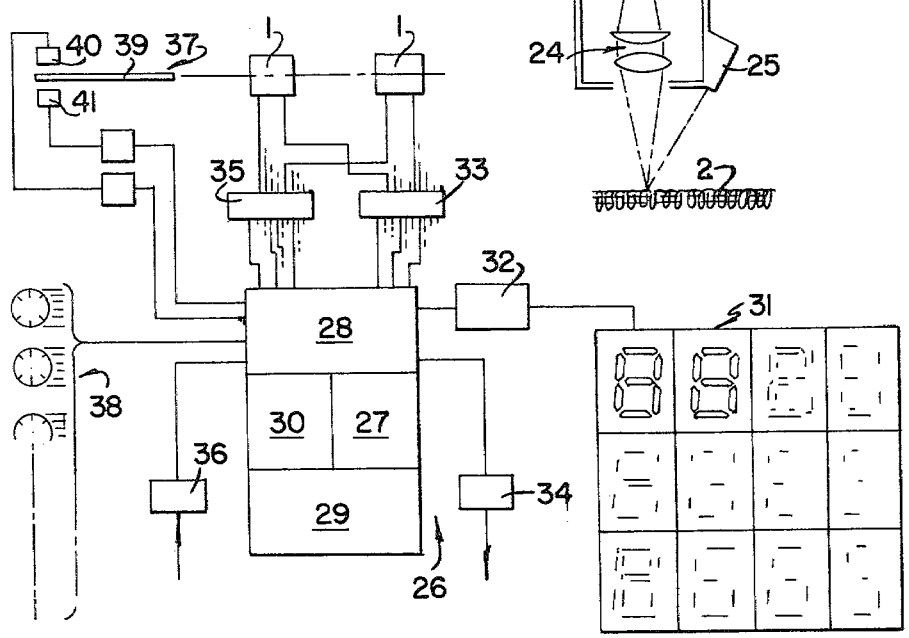
FIG. 6 is a block circuit diagram of the apparatus.

The light transmitters and receivers of the scanning devices 1 are connected via flexible leads to a monitoring system as shown in FIG. 6.

The monitoring system comprises a computing system 26 incorporating a microprocessor unit 27 with associated interface 28, memory (ROM and RAM) 29, and control and power supply devices 30. The computing system 26 has one output which controls operation of a bank of cathode ray tube numerical digital display devices 31 via a drive circuit 32. Each of the devices 31 is capable of displaying any selected numeral dependent on the signals fed to same. A further output is connected to a power supply control circuit 33 to which the transmitter leads of the different scanning devices 1 are connected; and a further output is connected to a data output feed device 34 (as described hereinafter). The computing system 26 has a first input which is connected to a pulse-shaping circuit 35 to which the receiver leads of the scanning devices 1 are connected, and further inputs are connected respectively to a control signal input device 36, a position coding device 37, and a code pre-setting device 38 all as described hereinafter.

The position coding device 37 comprises a plate which is fixed to the opposite end of the bar 5 to the cam drive 6. The plate 39 has a series of rows of holes therein and rows of light sources 40 and light receivers 41 are fixed at opposite sides of the plate in alignment with each other and with the positions of the holes. As the plate 39 moves backwards and forwards with the bar 5, the rows of holes move successively between the rows of light sources 40 and receivers 41, and selected ones of the receivers 41 receive light from the sources 40 through the holes in dependence on the pattern of holes in each row. Thus, successive different patterns of electrical signals are fed to the computing system 26 from the coding device 37 in correspondence with the movement of the scanning devices 1. The patterns of signals are in accordance with a code whereby each pattern is made up of a combination of 0 and 1 signals, and only one such signal changes (from 0 to 1 or 1 to 0 as appropriate) from one pattern to the next successive pattern.

The code pre-setting device 38 comprises a set of thumb wheels, one for each scanning device. Each thumb wheel has a set of contacts which can be connected in circuit in different combinations, depending on the setting of the thumb wheel, thereby to generate different binary codes which are fed to the computing system 26.

The control signal input device 36 can be connected to a remote control system to convey command instructions to the computing system 26 to release information stored in the memory thereof to the data output feed device 34.

In use, the computing system 26 controls the power supply device 33 to control the intensity of light emitted by the transmitter of the scanning device 1 so that the light intensity received by the receivers during normal reflection from the backing material is constant.

The receiver outputs of the scanning devices 1 are monitored by the computing system 26 and any departure from the norm as hereinbefore discussed is detected and an output signal is produced which actuates an alarm circuit (not shown) which operates a visual and-/or audible alarm and/or which acts to arrest operation of the tufting machine. At the same time a signal is fed to the drive device 32 to operate the display devices 31 to produce an illuminated display of a combination of numerals which identifies the position of the missing or misplaced or malformed yarn giving rise to the fault condition. The computing system 26 computes the appropriate combination of numerals on the basis of the identity of the code received from the position coding device 37 at the instant when the fault is detected and on the basis of the codes received from the code presetting device 38 which are preselected in accordance with the needle spacing for the tufting machine. The position of the light sources 40 and receivers 41 may be adjustable to enable compensation to be made for variation in width of the backing material.

The computing system 26 and display devices 31 may be mounted in a common housing which can be mounted on or alongside the tufting machine whereby, in a particularly convenient and advantageous manner, in the case where a fault is detected, a visual indication is produced alongside the machine which identifies the position of the fault.

Figure 7:
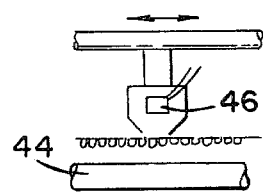
FIG. 7 is a diagrammatic sectional view of another scanning device.

The invention is not restricted to the details of the above embodiments which are described by way of example only. Thus, for example, instead of using scanning devices involving reflected light it is possible to use scanning devices involving transmitted light, for example comprising, as illustrated in FIG. 7, a common elongate light source 44 on one side of the material and a plurality of oscillating light receivers 46 on the opposite side thereof. In this case, it is to be noted that where a fault occurs which involves reciprocation of a needle having no yarn threaded therewith through the backing fabric the needle may in some cases produce an aperture in the fabric which is large enough to permit passage of light radiation therethrough whereby the radiation transmission properties of the fabric are of course dramatically changed; but in other cases an aperture may be produced which is very small or is virtually non-existent due to closing up of the fabric on retraction of the needle whereby radiation transmission properties are not so dramatically modified and reliance is had on change in translucence.

The invention is not limited to the context of tufted fabrics, since a like concept may be of interest in the inspection during (or even subsequent to) manufacture of other sheet materials.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus described the nature of the invention, what is claimed herein is:

1. Apparatus for detecting faults in an advancing sheet of fabric material comprising a radiation transmitter, means mounting said transmitter for directing radiation at one surface of said material, a plurality of detectors sensitive to the radiation transmitted by said transmitter for generating an electrical output representative thereof, mounting means including a support carrying said detectors for receiving radiation from said material, rigid cam drive means for drivingly oscillating said support a predetermined distance continuously in a linear path in a first transverse direction relatively to the direction of advancement of the material and then in the reverse direction, and monitoring means connected to said detectors for monitoring said electrical output to detect deviations from a norm, said cam drive means comprising a cam plate constrained for linear movement and a follower channel including first and second opposed cam surfaces, said surfaces being substantially transverse to said linear path, a rotatable disc, a follower eccentrically fastened to said disc and disposed in said channel, means for rotating said disc to force said follower successively against said first cam surface and then against said second cam surface to drive said cam plate, and means connecting said cam plate to said support.

2. In the apparatus recited in claim 1 wherein said scanning devices are spaced apart by a distance less than the distance each traverses, whereby the paths of movement of adjacent scanning devices overlap with each other.

3. In the apparatus as recited in claim 1 wherein said radiation transmitter comprises a plurality of transmitters, there being one transmitter corresponding to each detector, each transmitter and a corresponding detector are carried by a common housing, each said radiation transmitter comprising a light transmitter, said light transmitter being disposed in said housing at an angle to said sheet of material, said detector being disposed in said housing for receiving light reflected from said one surface of said material.

4. In the apparatus as recited in claim 1 wherein said radiation transmitter comprises a light transmitter, said mounting means including means for mounting each of said detectors at the opposite side of said material from said one surface and in disposition for receiving light from said light transmitter.

5. Apparatus as recited in claim 1, wherein said cam plate includes a pair of opposed cam tracks, and said disc includes a second follower fastened thereto and disposed for engagement with each of said tracks, said tracks being disposed such that said second follower engages one of the tracks when the first mentioned follower transitions from a first of said cam surfaces to the other, the engagement of said second follower with the track acting to initiate reversal of the cam direction.

6. Apparatus as recited in claim 5, wherein said cam plate comprises a body member having a substantially rectangular form, said cam tracks being convexly curved surfaces at two diametrically opposite corners of said plate, said follower channel being formed in a central region of said plate and defined about a central island.

* * * * *